US006291397B1

(12) United States Patent
Wilkins, Jr.

(10) Patent No.: US 6,291,397 B1
(45) Date of Patent: Sep. 18, 2001

(54) ALGAECIDE COMPOSITIONS AND METHODS OF REMOVING ALGAE

(76) Inventor: Joe S. Wilkins, Jr., 7700 Seawall Blvd., Unit 403, Galveston, TX (US) 77551

( * ) Notice: Subject to any disclaimer, the term of this patent is extended or adjusted under 35 U.S.C. 154(b) by 0 days.

(21) Appl. No.: 09/476,840

(22) Filed: Jan. 3, 2000

(51) Int. Cl.⁷ .......................... A01N 43/66; A01N 59/06; A01N 59/20
(52) U.S. Cl. ............................... 504/152; 504/155
(58) Field of Search ..................... 504/155, 152

(56) References Cited

U.S. PATENT DOCUMENTS

| | | | |
|---|---|---|---|
| 4,975,109 | 12/1990 | Friedman, Jr. et al. | 71/67 |
| 5,153,229 | 10/1992 | Chastain et al. | 514/763 |
| 5,164,109 | 11/1992 | Wojtowicz | 252/175 |
| 5,281,280 | 1/1994 | Lisowski et al. | 134/26 |
| 5,294,645 | 3/1994 | Chastain et al. | 514/729 |
| 5,373,025 | 12/1994 | Gay | 514/642 |
| 5,478,482 | * 12/1995 | Jones et al. | 510/753 |
| 5,614,528 | * 3/1997 | Jones et al. | 514/258 |
| 5,856,272 | 1/1999 | Wilkins, Jr. | 504/151 |
| 5,951,992 | 9/1999 | Wilkins, Jr. | 424/405 |

OTHER PUBLICATIONS

Product bulletin,—Quest Environmental Services, Inc.—"Mildew Removal" (facsimile date Feb. 28, 1996), 1 pg.
Stefan Company Product bulletin "Waterless Hand Cleaner based on Limonene" (Apr. 16, 1987)—1 pg.
Stefan Company Product bulletin "Limonene Based Waterless hadn cleaner" (Apr. 16, 1987)—1 pg.
Stella Mary Hass product bulletin "d–Limonene All–Purpose Cleaner" no date—1 pg.
DPC Industries, Inc. MSDS sheet (6 pages) (Nov. 6, 1986).
Van Waters & Rogers, Inc. MSDS sheet for Caustic Soda Anhydrous (Nov. 23, 1998)—1 pg.
MSDS sheet for 60 Chlorinating Composition (Feb. 27, 1995)—1 pg.
Asepsis, Inc./Hydrotech MSDS sheet for Hydrotech Granular Concentrate (Sep. 12, 1997)—3 pgs.
Chemtrec MSDS sheet for Lithium Hypochlorite (Dec. 22, 1998)—1 pg.

* cited by examiner

*Primary Examiner*—S. Mark Clardy
(74) *Attorney, Agent, or Firm*—Laura G. Barrow

(57) ABSTRACT

An algaecide formulated in a concentrated, solid composition form for subsequent dissolution in water is disclosed. The algaecide is designed to remove algae from a variety of interior and exterior surfaces. The preferred algaecide compositions chlorinated isocyanurates, such as sodium dichloro-s-triazinetrione, alkali hydroxides selected from the group consisting of sodium hydroxide, potassium hydroxide, calcium hydroxide, and lithium hydroxide; metal sulfates selected from the group consisting of copper sulfate, zinc sulfate, and aluminum sulfate; and a buffer.

14 Claims, No Drawings

ALGAECIDE COMPOSITIONS AND METHODS OF REMOVING ALGAE

BACKGROUND OF INVENTION

1. Field of Invention

The present invention is related to compositions for removing algae from a variety of surfaces.

2. Description of the Related Art

Especially in hot and humid environments, algae can grow on a variety of surfaces, both interior as well as exterior. The removal of algae from exterior as well as interior surfaces can be a time-consuming and rather unpleasant job, in particular where the surface area to be treated is rather large and/or exceptionally dirty with oil. A common algaecide is sodium hypochlorite. DPC Industries, Inc. of Houston, Tex. markets a useful algaecide composition, "DIXICHLOR", which consists of sodium hypochlorite, sodium chloride, sodium hydroxide, and water. Another algaecide composition, which was invented by the inventor of the present invention and the subject of U.S. Pat. No. 5,856,272 (and is incorporated by reference herein in its entirety) is currently marketed by Magnum Cleaning Products (Galveston, Tex.) as MAGNACHLOR. MAGNACHLOR contains about 10% sodium hypochlorite. To the best of the inventor's knowledge, most if not all algaecide agents on the market comprise sodium hypochlorite, which is believed to be necessary in eradicating algae.

Sodium hypochlorite, while an excellent algaecidal agent, can be hazardous to work with. The compound reacts vigorously with sodium hydroxide, for example, resulting in noxious fumes that are very irritating to the user's eyes, causing blurring and tearing. The compound may also cause skin irritation as well as irritation to sensitive mucousal membranes of the mouth and nose when inhaled.

Most algaecidal agents are formulated and marketed as liquids; however, such liquid formulations have certain undesirable disadvantages, notwithstanding their overall effectiveness in eradicating algae. For example, liquid algaecidal agents comprising sodium hypochlorite have limited shelf lives, generally ranging from six to eight months. Transportation of liquid formulations can also be expensive and hazardous if large quantities of the algaecidal composition are desired (generally, a gallon solution comprises about 10% of sodium hypochlorite). Conversely, a concentrated algaecidal solid formulation can be more easily shipped, and more importantly, has an indefinite shelf-life, since the solid compounds comprising the solid formulation would not be activated until mixed in water or other suitable liquid carrier.

It would therefore be desirable to have an algaecide formulated in a concentrated solid that, just prior to use, can simply be mixed with water or other suitable liquid carrier in a single step. While sodium hypochlorite is available in solid form, it will not work effectively alone if mixed in water and then applied to an algae-covered surface. Moreover, combining sodium hypochlorite and sodium hydroxide in solid form will not effectively kill the algae, since this combination, at the desired algaecidal percentages (about 10% sodium hypochlorite and 1% sodium hydroxide) exceeds the solubility of sodium hypochlorite, thereby resulting in the sodium hypochlorite falling out of solution upon mixing.

SUMMARY OF THE INVENTION

The present invention is related to novel algaecidal solid mixtures that may be mixed, in one step, with water just prior to application onto an algae-covered surface. The algaecidal mixture and resulting solution is less hazardous to work with compared to other algaecidal agents on the market, is easier and less expensive to transport in solid form, and has an indefinite shelf-life in solid form, as well.

Specifically, the present invention is directed to compositions comprising a combination of alkali hydroxides, such as sodium hydroxide, potassium hydroxide, and lithium hydroxide; a metal sulfate such as aluminum sulfate, calcium sulfate, and zinc sulfate; and chlorinated isocyanurates, preferably sodium dichloro-s-triazinetrione. The present invention is also directed to a method of removing algae from a variety of surfaces and comprises applying an algaecidal solution to an algae-covered surface, followed by a water rinse after a time sufficient to allow the algaecidal solution to kill the algae. The algaecidal solution comprises the components of the algaecidal mixture, namely a combination of alkali hydroxides, such as sodium hydroxide, potassium hydroxide, calcium hydroxide, and lithium hydroxide; a metal sulfate such as aluminum sulfate, calcium sulfate, and zinc sulfate; and chlorinated isocyanurates, preferably sodium dichloro-s-triazinetrione. The algaecidal composition further includes a buffer to prevent the components from falling out of solution after mixing in water while at the same time allowing the chlorine that results upon dissolution to be released after about 12 hours post-solution. A preferred buffer comprises about 25 to 30% of an alkali hypochlorite, preferably lithium hypochlorite. A buffer vended by VanWaters & Rodgers, Inc. comprises lithium hypochlorite (25–30%), sodium chloride (36%), sodium sulfate (13%), potassium sulfate (6%), lithium chloride (4%), lithium chlorate (2%), lithium hydroxide (1%), and water (7%).

The present invention is also directed to a method of removing algae comprising (1) combining an algaecidal mixture, comprising, in solid form, alkali hydroxides, such as sodium hydroxide, potassium hydroxide, calcium hydroxide, and lithium hydroxide; a metal sulfate such as aluminum sulfate, calcium sulfate, and zinc sulfate; chlorinated isocyanurates, preferably sodium dichloro-s-triazinetrione; and a buffer comprising an alkali (e.g. lithium) hypochlorite; (2) mixing the algaecidal mixture with water to form an algaecidal solution; (3) applying the algaecidal solution to a surface having evidence of algae growth; and (4) rinsing the treated surface with water or other aqueous liquid.

DETAILED DESCRIPTION OF THE PREFERRED EMBODIMENTS

The inventive algaecidal composition is a concentrated solid mixture of alkali hydroxides, chlorinated isocyanurates, metal sulfates, and a buffer. A preferred chlorinated isocyanurate is sodium dichloro-s-triazinetrione, vended by Asepsis Inc. (Avondale Estates, Georgia) as HYDROTECH GRANULAR CONCENTRATE. The isocyanurates function as the primary algaecidal agent. In the preferred embodiment, the solid concentrated mixture comprises an amount of sodium dichloro-s-triazinetrione such that in solution, the resulting algaecidal solution comprises from about 3.5 to about 20 w/w % of the sodium dichloro-s-trianzinetrione, depending upon the desired algaecide solution strength. The solid mixture comprises about 36% of alkali dichloro-s-triazinetrione.

The inventive mixture also includes an alkali hydroxide, preferably sodium hydroxide, which comprises from about 2 to 12 w/w % of the resulting algaecidal solution (the solid mixtures comprises about 62% of the alkali hydroxide). Other alkali metals, such as potassium or lithium, may be employed, as well. The sodium hydroxide is present to disintegrate the algae from at its root, and further aids in algae removal up and away from the treated surface by a "bubbling" action similar to that of hydrogen peroxide.

Preferably, the inventive algaecide mixture contains a component to inhibit future algae growth. A suitable algae-growth inhibitor is a metal sulfate, such as copper sulfate, aluminum sulfate, and zinc sulfate. [Only one of the sulfates should be used in a given formulation] A preferred percentage of metal sulfate in the algaecidal solution is at least about 0.012 w/w % (the solid mixture comprises about 0.2% of the metal sulfate).

The inventive algaecide mixture further includes a buffer to prevent the components from falling out of solution. A preferred buffer comprises an alkali hypochlorite, such as lithium hypochlorite. A preferred buffer vended by VanWaters & Rodgers, Inc. comprises lithium hypochlorite (25–30%), sodium chloride (36%), sodium sulfate (13%), potassium sulfate (6%), lithium chloride (4%), lithium chlorate (2%), lithium hydroxide (1%), and water (7%). The buffer comprises about 2% of the solid mixture, with the alkali (e.g. lithium) hydroxide comprising from 0.4 to 0.5 w/w % of the solid mixture). It will be understood and appreciated by those of ordinary skill in the art that the present invention is not limited to an algaecide mixture comprising the preferred buffer described herein, and that any suitable buffer may be employed that will serve the same function.

The algaecide solid mixture contains a 1.7 to 1 ratio of sodium dichloro-s-triazinetrione to sodium hydroxide in amounts such that, in combination with the metal sulfate and buffer, the algaecidal solid mixture comprises from about 5.5 to 33 w/w %, of the final algaecidal solution, depending upon the desired strength.

In preparing the inventive concentrated algaecide mixture, no special equipment is needed. When the solid components are combined, the resulting mixture may later be poured into a container of water or other suitable aqueous carrier prior to use and mixed until the components are in solution (i.e. the solution turns from a cloudy, light green color to a substantially clear, light green solution when viewed by the naked eye, this transition taking about approximately one to two minutes, while stirring). The resulting algaecidal solution can then be poured into a spray bottle, for example, for subsequent application to an algae-covered surface. [For optimal results, the solution should be used within 24 hours of reconstitution] The solution should be allowed to remain on the treated surface for about 20 to 30 minutes, after which time the treated surface may be rinsed with water using a simple garden hose (at higher concentrations of dichloro-s-triazinetrione, the time between surface application and rinsing may be less). An advantage of the present invention is that algae may be fully eradicated and removed from the treated surface without necessitating the added use of a pressure spray gun, either for application of the solution or rinsing.

While the preferred embodiment of the present invention is directed to adding a concentrated algaecidal solid mixture of the components described above, those of ordinary skill in the art will appreciate that, if desired, the individual solid components may be added to the water separately, prior to treatment, although this is the less desirable method from a commercial stand-point.

The present inventive is advantageous over other liquid based algaecidal products in that its shelf life, in solid form, is essentially indefinite. Moreover, the more hazardous sodium hypochlorite has been eliminated entirely, thus making the resulting algaecidal solution less irritating to work with. And while the time for algae removal may be slightly longer with the algaecidal solution manufactured from the inventive algaecidal solid as compared to sodium hypochlorite algaecides (i.e. 20 to 30 minutes verses 10 to 15 minutes for DIXICHLOR), the ultimate algaecidal effectiveness (i.e. complete algae eradication from the treated surface) is the same. As noted above, killing time may be decreased if higher levels of sodium dichloro-s-triazinetrione are used, resulting in maximum chlorine amounts comprising about 62% to 65% of the algeacide solid mixture.

The present inventive algaecide mixture works well on concrete, pavement, wood, tile, porcelain, vinyl, brick, stucco, fiberglass, and aluminum surfaces. These surfaces may be painted or unpainted. To treat large algae-covered surfaces such as patios, swimming pools, boats and other vehicles, floors, and walls, for example, about 1 gallon of the inventive composition per about 100 square feet is applied, preferably by spraying, to the surface. The composition should be allowed to remain on the surface for at least 15 minutes, more preferably for about 15 to 30 minutes, afterwards it may be washed off with water. As stated above, it is not necessary to apply the water under pressure by using, for example, a pressure spray gun. Rather, a simple garden hose may be used.

Other suitable surfaces include, but are not limited to, basins, showers, bathtubs, and toilet bowls and tanks. In treating the foregoing and similar fixtures, about 1 gallon of the resulting algaecide solution per about 100 square feet should be used. The inventive algaecidal solution should preferably remain on the treated surface for a time period ranging from about 15 to about 30 minutes, and afterwards it may washed off with water.

The following examples are not intended to limit the scope of the invention, but are intended to illustrate the various aspects of the invention.

EXAMPLE 1

An eight-ounce mixture of algaecide was made by mixing 144 grams of sodium dichloro-s-trianzinetrione with 84 grams of sodium hydroxide, 0.4 gram of copper sulfate, and 4 grams of "lithium hypochlorite" buffer vended by Van-Waters and Rodgers comprising 25% to 30% lithium hypochlorite (and other components as described earlier in this specification) to form a mixture granules/beads. The mixture was then added to 1 gallon of water, with stirring, until clear, about one to two minutes. The solution was sprayed onto an algae-covered concrete surface for about minutes. The solution was then removed with a non-pressurized water rinse. After about 6 months, no algae growth was observed.

EXAMPLE 2

A concentrated algaecidal solid composition was prepared as described in Example 1, except aluminum sulfate was used instead of copper sulfate.

EXAMPLE 3

A concentrated algaecidal solid composition was prepared as described in Example 1, except zinc sulfate was used instead of copper sulfate.

EXAMPLE 4

A concentrated algaecidal solid composition was prepared as described in Example 1, except potassium hydroxide was used instead of sodium hydroxide.

EXAMPLE 5

A concentrated algaecidal solid composition was prepared as described in Example 1, except lithium hydroxide was used instead of sodium hydroxide.

EXAMPLE 6

The algaecidal solid composition was prepared as described in Example 1 and added to 1 pint of water, with stirring, until clear, about one to two minutes. The solution was sprayed onto an algae-covered concrete surface for about 15 minutes. The solution was then removed with a non-pressurized water rinse. After about 6 months, no algae growth was observed.

EXAMPLE 7

The algaecidal solid composition was prepared as described in Example 1 and added to 1 pint of water, with stirring, until clear, about one to two minutes. The solution was sprayed onto an algae-covered vinyl surface for about 15 minutes. The solution was then removed with a non-pressurized water rinse. After about 6 months, no algae growth was observed.

I claim:

1. A method of removing algae from surfaces comprising:
   (a) Applying an algaecidal solution to a surface having evidence of algae growth, said solution comprising chlorinated isocyanurates; alkali hydroxides selected from the group consisting of sodium hydroxide, potassium hydroxide, calcium hydroxide, and lithium hydroxide; a metal sulfate selected from the group consisting of copper sulfate, zinc sulfate, and aluminum sulfate; and a buffer; and
   (b) rinsing said surface with water after a time sufficient to allow said algaecidal solution to eradicate said algae.

2. The method of claim 1, wherein said chlorinated isocyanurates is sodium dichloro-s-triazinetrione.

3. The method of 2, wherein said alkali hydroxide is sodium hydroxide.

4. The method of claim 2, wherein said buffer is an alkali hypochlorite selected from the group consisting of lithium hypochlorite, sodium hypochlorite, calcium hypochlorite, and potassium hypochlorite.

5. The algaecide solution of claim 4, wherein said alkali hypochlorite is lithium hypochlorite.

6. The method of claim 1, wherein said solution comprises 3 w/w % to 20 w/w % said sodium dichloro-s-triazinetrione, 2 w/w % to 12 w/w % of said alkali hydroxides, and at least 0.01 w/w % of said metal sulfate.

7. The method of claim 6, wherein said alkali hydroxide is sodium hydroxide.

8. The method of claim 7, wherein said alkali hydroxide is sodium hydroxide.

9. A method of removing algae from surfaces comprising:
   (a) Combining a solid algaecidal mixture with water to form an algaecidal solution, said mixture comprising chlorinated isocyanurates; alkali hydroxides selected from the group consisting of sodium hydroxide, potassium hydroxide, calcium hydroxide, and lithium hydroxide; a metal sulfate selected from the group consisting of copper sulfate, zinc sulfate, and aluminum sulfate; and a buffer;
   (b) applying said algaecidal solution to a surface having evidence of algae growth; and
   (c) rinsing said surface with water after a time sufficient to allow said algaecidal solution to eradicate said algae.

10. The method of claim 9, wherein said chlorinated isocyanurates is sodium dichloro-s-triazinetrione.

11. The method of 9, wherein said alkali hydroxide is sodium hydroxide.

12. The method of claim 10, wherein said solution comprises 3 w/w % to 20 w/w % of said sodium dichloro-s-triazinetrione, 2 w/w % to 12 w/w % of said alkali hydroxides, and at least 0.01 w/w % of said metal sulfate.

13. The method of claim 10, wherein said alkali hydroxide is sodium hydroxide.

14. The method of claim 13, wherein said alkali hydroxide is sodium hydroxide.

* * * * *